(12) United States Patent
Stump et al.

(10) Patent No.: US 8,437,847 B2
(45) Date of Patent: May 7, 2013

(54) BATTERY COMPARTMENT FOR AN EXTERNAL PACEMAKER

(75) Inventors: Joachim Stump, Berlin (DE); Enrico Brzank, Berlin (DE); Konrad Weber, Berlin (DE); Peter Grund, Berlin (DE); Oliver Krips, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 379 days.

(21) Appl. No.: 12/724,917

(22) Filed: Mar. 16, 2010

(65) Prior Publication Data

US 2010/0241187 A1    Sep. 23, 2010

(30) Foreign Application Priority Data

Mar. 17, 2009   (DE) .................. 10 2009 001 611

(51) Int. Cl.
*A61N 1/38* (2006.01)
(52) U.S. Cl.
USPC ............................................................. 607/5

(58) Field of Classification Search .................. 607/2, 9, 607/4, 5
See application file for complete search history.

(56) References Cited

U.S. PATENT DOCUMENTS 5,637,417 A * 6/1997 Engmark et al. ................ 429/97
6,980,859 B2   12/2005 Powers et al.

OTHER PUBLICATIONS

German Search Report, dated Jan. 21, 2010 (2 pages).

\* cited by examiner

*Primary Examiner* — Scott Getzow
*Assistant Examiner* — Amanda Patton
(74) *Attorney, Agent, or Firm* — Buchanan Ingersoll & Rooney PC

(57) ABSTRACT

A pacemaker comprising a battery compartment displaceable between a removal position and an operating position along a first direction of displacement for receiving a replaceable battery having a first and a second battery pole disposed on a battery face. The battery compartment comprises an electrically isolating partial cover, which is disposed on a second side opposite the first side and designed to cover a base of the battery directed toward the second side in the direction of the removal side of the battery compartment.

11 Claims, 4 Drawing Sheets

BATTERY COMPARTMENT FOR AN EXTERNAL PACEMAKER

CROSS-REFERENCE TO RELATED APPLICATIONS

This application claims the priority of German Patent Application No. DE 10 2009 001 611.2, filed on Mar. 17, 2009 in the German Patent Office, the disclosure of which is incorporated herein in its entirety by reference.

FIELD OF THE INVENTION

The present invention relates to an external pacemaker comprising a battery compartment, which allows a replaceable battery for the operation of the external pacemaker to be received.

BACKGROUND OF THE INVENTION

External pacemakers can be used for the transcutaneous stimulation of the heart. Likewise, it is possible to perform intracardiac stimulation using an external pacemaker and an electrode which is introduced into the heart through a vein. In both instances, however, the external pacemaker generally constitutes only a temporary solution because the treatment is associated with undesirable side effects, such as an undesirable stimulation of other muscle tissue located in the vicinity of the heart, for example, the rib muscles, or an increased risk of infection. On the other hand, compared to implantable pacemakers, external pacemakers offer the obvious advantage that a replacement of parts or of the entire pacemaker is possible without difficulty.

In particular, the battery used for operating the external pacemaker can be replaced, while, in the case of an implanted pacemaker, this is possible only within the context of surgery and replacement of the entire device. External pacemakers are subject to standard specifications, which are intended to ensure fast replacement of the battery and reliable operation of the pacemaker at the same time. In particular, one of the concerns is to provide a mechanism which is easy to operate and secured to prevent inadvertent opening, such as when being dropped. This is important, because the hospital staff must also replace the battery under time constraints and without specific training. In addition, it is to be ensured that the battery cannot be touched until the battery poles have a certain distance from the contacts of the pacemaker.

From U.S. Pat. No. 5,637,417, an external pacemaker comprising a battery drawer is known, which allows a replaceable battery to be received. The battery drawer is opened by pushing a button on the outside of the pacemaker housing, thereby actuating a release mechanism. This has the disadvantage that the battery drawer may open if the external pacemaker is dropped. In addition, the mechanism is not self-explanatory because the button for opening the drawer is provided in a different location of the pacemaker than the location at which the battery drawer opens. In addition, due to the release mechanism, the battery can inadvertently fall out of the battery drawer, as it is not apparent while pressing the button which way the pacemaker must be held, so that the removal side of the battery drawer may be pointed downward at the time it is released. Another disadvantage of the pacemaker disclosed in U.S. Pat. No. 5,637,417 is the contacting of the battery, which is implemented by spring contacts. The present invention is directed toward overcoming one or more of the above-identified problems.

SUMMARY OF THE INVENTION

It is therefore an object of the present invention to provide a secure mechanism for replacing a battery of an external pacemaker that enables reliable contacting of the battery.

It is a further object of the present invention to provide a mechanism for opening the battery compartment that is easy and quick to operate.

For these reasons, the invention proposes a pacemaker having a pacemaker housing. The pacemaker housing comprises a recess in which a battery compartment is disposed displaceable between a removal position and an operating position along a first direction of displacement. The battery compartment allows a battery having a first and a second battery pole provided on a battery face, preferably a 9V block (battery), to be received and replaced through a removal side (top) of the battery compartment. In the removal position, the battery compartment is pulled entirely or partially out of the pacemaker such that the battery can be removed through the removal side of the battery compartment and replaced. In the operating position, the battery compartment is inserted back into the pacemaker, which can then resume operation with the new battery. The pacemaker further comprises means for locking the battery compartment in the operating position.

On a first side oriented in the first direction of displacement, the battery compartment has at least one first slot, which is open toward the removal side of the battery compartment and positioned on the first side such that it allows contacting of the battery from outside of the battery compartment. The first side of the battery compartment, however, is directed toward the inside of the pacemaker, thereby enabling contacting from outside of the battery compartment, but only from inside the pacemaker.

According to the present invention, the battery compartment comprises an electrically isolating partial cover, which is disposed on a second side opposite the first side and designed to cover a base of the battery directed toward the second side in the direction of the removal side of the battery compartment. The partial cover ensures that the battery compartment must first be pulled out of the pacemaker a certain length before the battery located in the battery compartment can be touched. However, if the battery compartment is pulled this far out of the pacemaker, the distance between the battery contacts disposed in the pacemaker and the battery poles of the battery is already large enough to ensure safe electrical isolation of the battery from the electronics of the pacemaker. In addition, the partial cover has the advantage that it prevents the battery from falling out should the pacemaker open inadvertently, because the battery compartment must be pulled completely out of the pacemaker in order to remove the battery.

In one embodiment, the battery compartment has a first tension spring disposed on the second side, the first tension spring being designed to exercise a first spring force on the battery along the first direction of displacement. As a result of this spring force, the inserted battery is pushed against the first side of the battery compartment, whereby the battery is fixed in the removal position to a certain degree inside the battery compartment.

In a preferred embodiment of the invention, the pacemaker comprises a contact carrier, which is fastened in the pacemaker housing and mounted pivotally about a pivot axis and which on a surface opposite the (outside of the) first side of the battery compartment has a first and a second contact on opposing sides of the pivot axis. The contact carrier is disposed such that the first and the second battery pole contact one of the first and the second contact in the operating position of the battery compartment. Since the contact carrier is pivotally suspended, the action of force of the first and second battery poles which are pushed against the first and second contacts is uniformly distributed among both contact battery pole pairs, thereby ensuring good contacting. Contrary to the known spring contacts, the first tension spring, which pushes the battery against the contacts, is not limited by the dimensions of the battery poles and by the function as an electric contact and can therefore be designed accordingly stable and reliable.

In one embodiment of the pacemaker, the first slot has a first diameter and a second diameter, wherein the second diameter is smaller than the first diameter. The first slot has the first diameter at a first point and the second diameter at a second point. The first point is disposed at a lesser distance from the removal side than the second point. The first slot thus tapers from the opening of the first slot toward the removal side of the battery compartment to the end of the slot. During insertion, this allows positioning of the battery poles with little accuracy, which is automatically compensated for by the taper of the first slot when the battery glides into the battery compartment. The position of the battery is therefore subjected to self-adjustment in this embodiment of the inventive pacemaker.

In a particularly preferred embodiment, the second diameter is larger than a diameter of the first battery pole and smaller than a diameter of the second battery pole. In addition, the first diameter is larger than the diameter of the first battery pole and larger than the diameter of the second battery pole. As a result of this simple measure, it is possible to avoid a mix-up of the battery poles, which have different diameters in a 9V block (battery), for example, since the pole having the larger diameter cannot be pushed to the end of the first slot since the diameter of the first slot is not large enough there to receive the larger pole.

Alternatively, on the first side of the battery compartment the pacemaker may comprise a second slot which is open toward the removal side of the battery compartment. The first and second slots are positioned on the first side such that they allow contacting of the first or second battery pole from outside of the battery compartment. In this variant, a separate slot is provided for each battery pole of the battery.

The first slot preferably has a third diameter, and the second slot has a fourth diameter, wherein the fourth diameter is smaller than the third diameter.

Advantageously, the fourth diameter is larger than a diameter of the first battery pole and smaller than a diameter of the second battery pole. In addition, the third diameter is larger than the diameter of the second battery pole. This variant comprising two slots for contacting the battery has the advantage explained above that due to the smaller diameter of the first slot, which consequently does not allow the larger second battery pole to be received, incorrect insertion of the battery is excluded.

A further concept of the present invention, which can also be implemented independently, relates to a pacemaker, wherein the battery compartment on the second side has a second tension spring and a handle which can be displaced along a second direction of displacement intersecting the first direction of displacement. The second tension spring is designed to exercise a spring force on the handle along the second direction of displacement. The recess of the pacemaker housing and the handle comprise at least one groove and a spring. It does not matter whether the groove is disposed on the recess and the spring on the handle, or whether the spring is disposed on the recess and the groove on the handle. The groove has a closed part and a part which is open in the first direction of displacement. The spring can be guided in the groove (can be displaced guided by the groove) and is disposed, or can be disposed, such that the second tension spring exercises a second spring force on the handle when the spring is located in the open part of the groove, and exercises a third spring force on the handle when the spring is located in the closed part of the groove. The second spring force is greater than the third spring force. By displacing the handle against the action of force of the second tension spring such that the spring is displaced into the open part of the groove, the spring can be moved out of the groove by displacing the battery compartment in the first direction of displacement through the opening of the open part of the groove, whereby the battery compartment can be displaced freely along the first direction of displacement. If, however, the spring is located in the closed part of the groove, the battery compartment is retained in the operating position because the spring strikes against the wall of the closed part of the groove. This embodiment can be designed for batteries having only a single pole on the face of the battery, even without the pivotal contact carrier.

An embodiment of the inventive pacemaker in which a connecting line from the open part of the groove to the closed part of the groove has a direction component in the first direction of displacement is particularly preferred. In this way, the second tension spring is designed to move the battery compartment into the operating position due to the action of force of the spring on the handle and the resulting movement of the spring into the closed part of the groove, which is to say to automatically close the battery compartment.

All embodiments of the pacemaker may have a sealing ring surrounding the second side of the battery compartment, the ring being designed to seal the recess of the pacemaker housing when the battery compartment is in the operating position. In this way, the battery and the electronics of the pacemaker are protected from penetrating moisture.

BRIEF DESCRIPTION OF THE DRAWINGS

The present invention will be explained in more detail hereinafter based on several illustrations.

DETAILED DESCRIPTION OF THE INVENTION

Figure 1A:
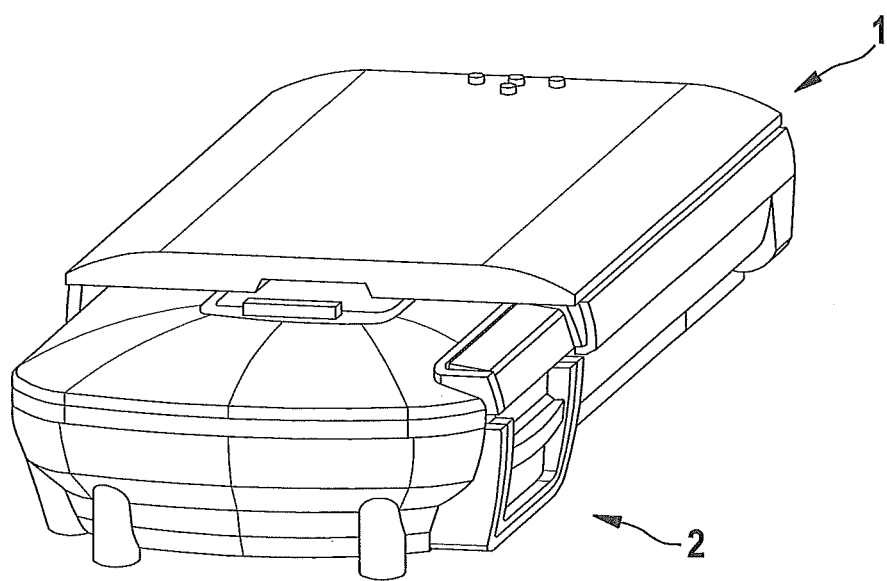
FIG. 1 shows a pacemaker according to the present invention in two partial illustrations (FIGS. 1a and 1b)
Figure 1B:
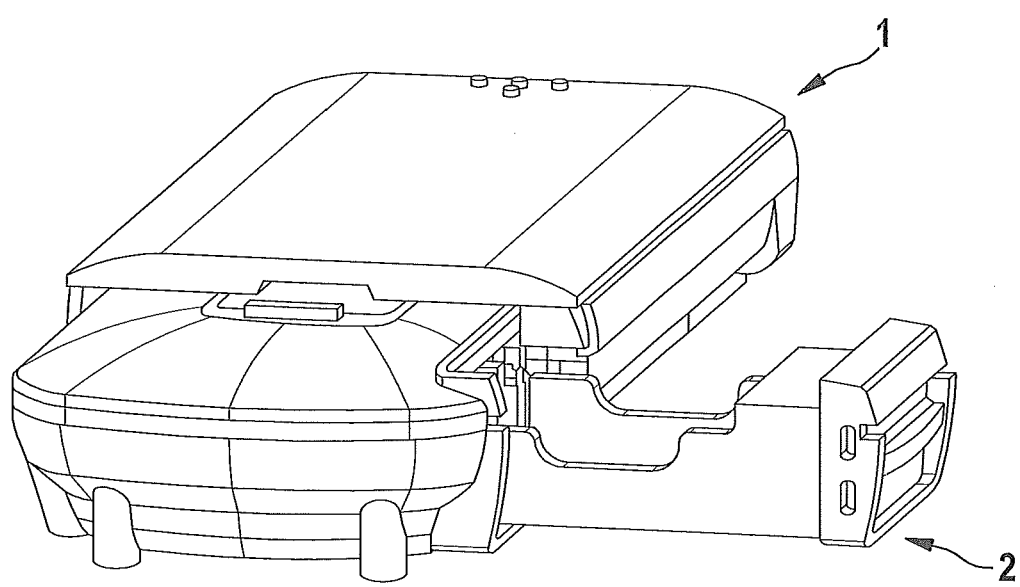

FIG. 1 shows a pacemaker 1 according to the present invention in two partial illustrations (a) and (b). The pacemaker 1 comprises a battery compartment 2, which in partial illustration FIG. 1a is shown in the operating position, which is to say inserted into the pacemaker and locked, and in partial illustration FIG. 1b is shown in the removal position, which is to say pulled out of the pacemaker 1. The battery compartment 2 offers room for a replaceable battery 3, preferably a 9V block (battery), which can be placed into the battery compartment 2 through the removal side of the battery compartment 2 (top side). A first spring, which is disposed in the battery compartment 2 on the side away from the inside of the pacemaker 1, is not shown. This first tension spring is designed to exercise a spring force onto an inserted battery 3 and press it in the direction of the interior of the pacemaker 1. However, embodiments of the pacemaker without a first tension spring are also possible.

Figure 2A:
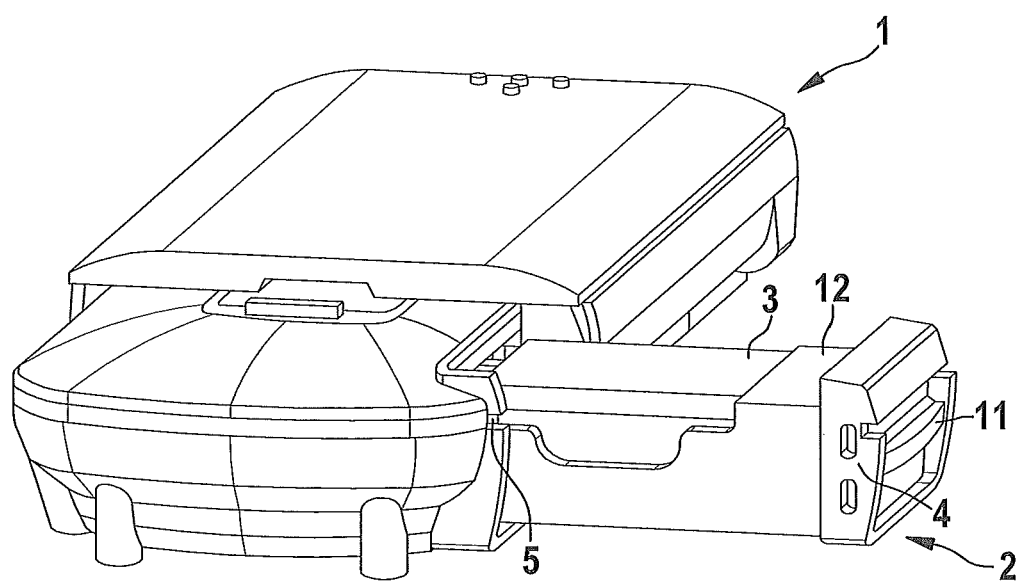
FIG. 2 illustrates removal of a battery from the pacemaker according to the present invention based on two partial illustrations (FIGS. 2a and 2b)
Figure 2B:
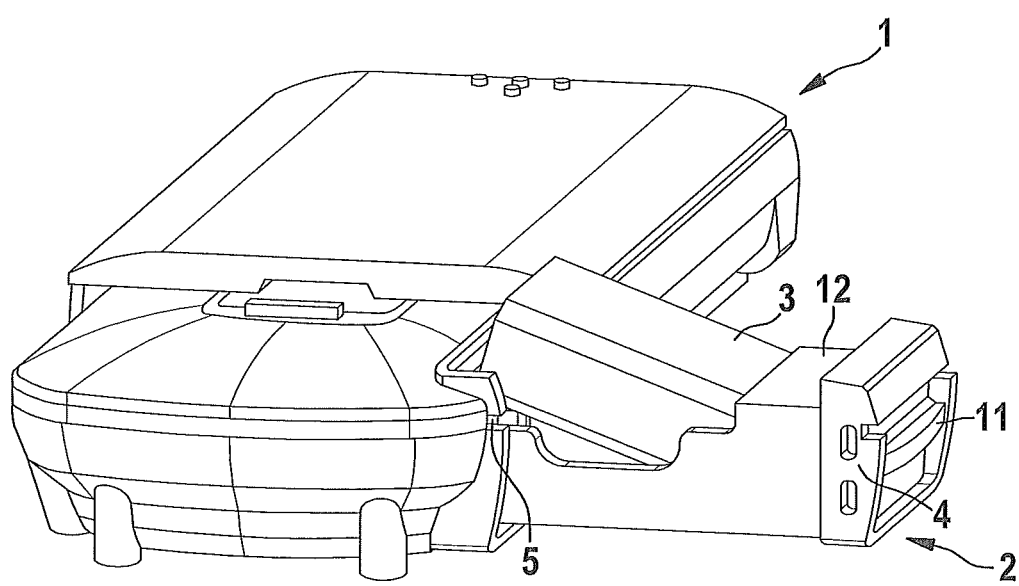

FIG. 2 illustrates the removal of a battery from the pacemaker 1 according to the present invention based on two partial illustrations (a) and (b). In partial illustration FIG. 2a, the battery compartment 2 of the pacemaker 1 is already opened. The battery 3 to be removed is located in the battery compartment 2. It is apparent from partial illustration FIG. 2b how the battery 3 is lifted out of the battery compartment 2 using a rotary motion. With a partial cover 12 on the removal side of the battery compartment 2, the invention ensures that removal of the battery 3 is impossible until the battery compartment 2 is pulled completely out of the pacemaker 1. Due to the partial cover 12, the base of the battery 3 cannot be removed from the battery compartment before the top of the battery 3. This prevents the battery 3 from falling out when the battery compartment 2 is inadvertently partially opened. It is furthermore ensured in this way that the battery 3 is located far enough away from the battery contacts located inside the pacemaker 1 and that the contact is not reestablished by tilting the battery 3 about the top thereof when lifting the base. In addition, the battery 3 cannot be touched while opening the battery compartment 2. Contact with the battery 3 is not possible until the battery compartment 2 has been pulled sufficiently out of the pacemaker 1 and the battery contacts disposed in the pacemaker housing are an appropriate distance from the battery 3.

The partial illustrations from FIG. 2 furthermore indicate a spring 4 and a groove 5. The spring 4 is connected to a handle 11 disposed on the front (second side) of the battery compartment 2. In the figure, the handle 11 can be displaced in the vertical direction, whereby the spring 4 is displaced accordingly in a guide in the wall of the battery compartment 2. A second tension spring, which is disposed in the front of the battery compartment 2, is not visible in the partial illustrations of FIG. 2. The second tension spring exercises a spring force on the handle 11 such that the handle takes on a resting position and can be displaced into a second handle position only by applying a certain force.

The groove 5 is shaped such that the spring 4 can be moved therein. The groove 5 is open in an open part toward the front of the pacemaker 1 and placed such that the spring 4 can be moved into or out of the groove 5 through the opening thereof when the handle 11 is located in the second handle position. In addition, the groove 5 has a closed part, which is disposed relative to the open part of the groove 5 such that the spring 4 is located in the closed part of the groove 5 when the handle 11 takes on the resting position and the battery compartment 2 is pushed into the pacemaker 1 (operating position). Since the spring 4 in this case is located in the closed part of the groove 5, the battery compartment 2 cannot be pulled out of the pacemaker 1 unless the handle 11 is displaced. This is only possible in that the handle 11 is displaced counter to the action of force of the second tension spring and the battery compartment 2 is pulled out of the pacemaker 1 at the same time. The means for locking the battery compartment 2 in the operating position formed by the spring 4, groove 5, and handle 11 can also be implemented as concepts separate from the remaining concepts of the invention.

Figure 3:
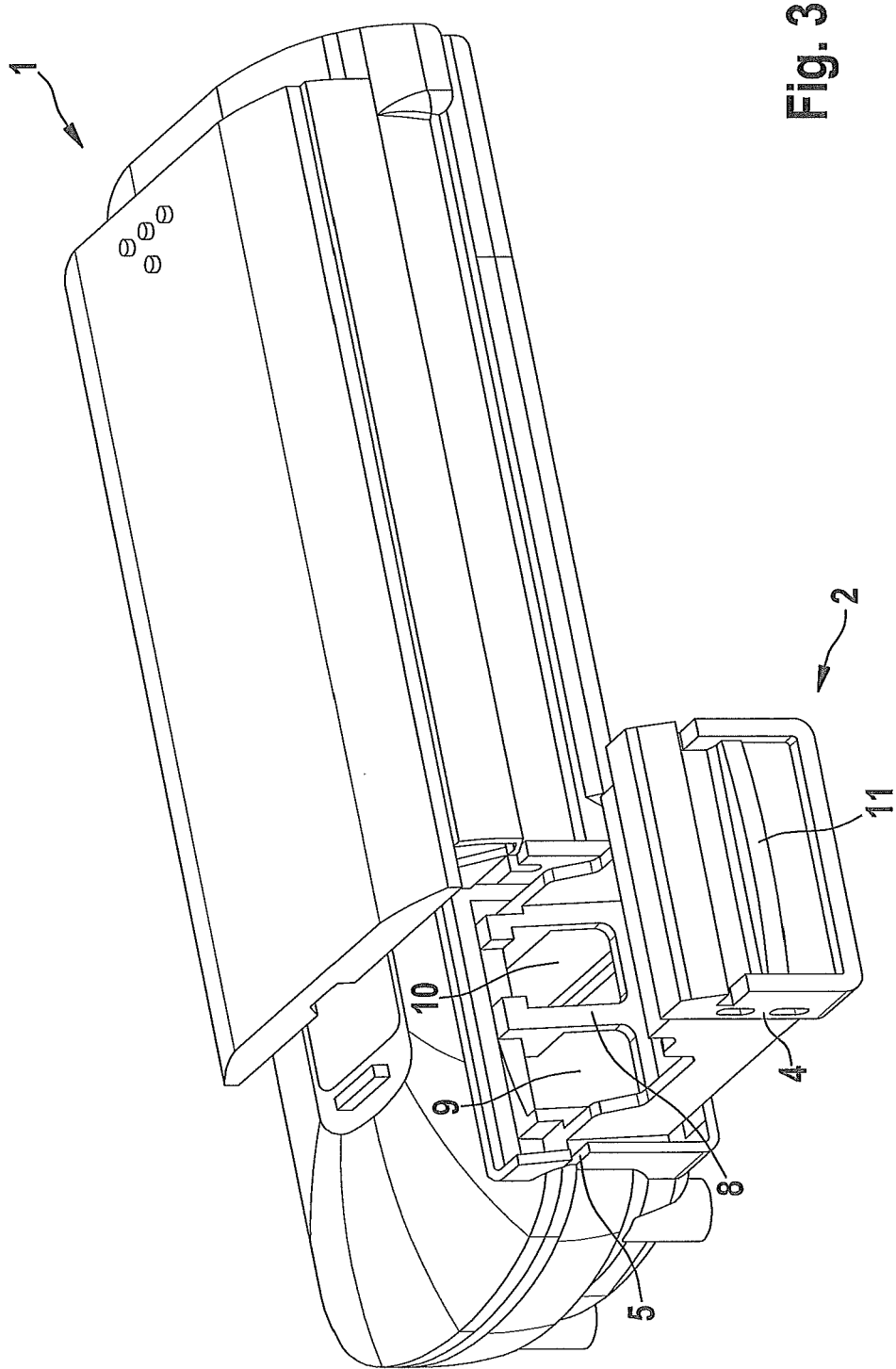
FIG. 3 shows the pacemaker according to the present invention in an oblique top view.

FIG. 3 shows the pacemaker according to the invention in an oblique top view. Again, the spring 4 and groove 5 can be seen. Also apparent are a first slot 9 and a second slot 10, which have different diameters from each other in the upper part. The first and second slots 9, 10 are disposed in the first wall 8 of the battery compartment 2 directed toward the interior of the pacemaker 2 and allow contacting of the poles of a battery 3 inserted in the battery compartment 2 from inside the pacemaker 1.

Figure 4:
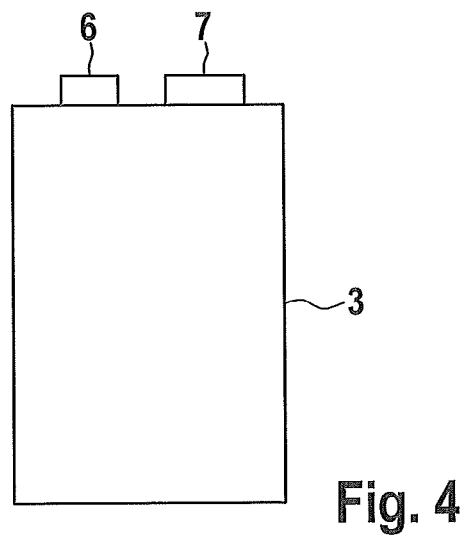
FIG. 4 is a schematic illustration of a commercially available 9V block (battery)

FIG. 4 shows a schematic side view of a commercially available 9V block (battery) 3. A first battery pole 6 and a second battery pole 7 are disposed on a battery face. It is clearly apparent that the first battery pole 6 has a smaller diameter than the second battery pole 7.

Figure 5:
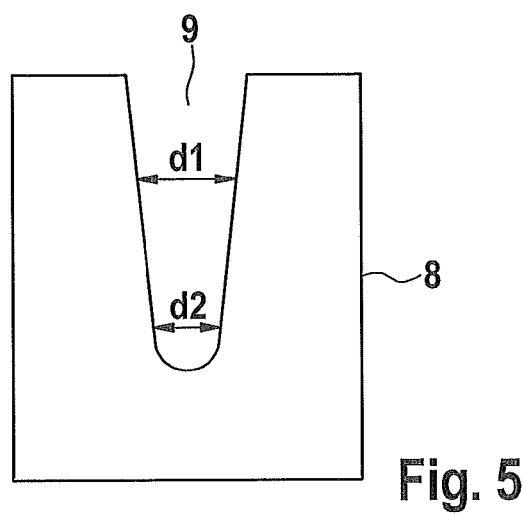
FIG. 5 shows a first side of the battery compartment in an embodiment having only one slot.

FIG. 5 shows a first side 8 of the battery compartment in an embodiment having only one slot. The first slot 9 has different diameters along the course thereof and tapers toward the bottom of the battery compartment 2. Diameter d2 is larger than the diameter of the first battery pole 6, but smaller than the diameter of the second battery pole 7. Diameter d1, on the other hand, is larger than the two diameters d1, d2. In this way, it is ensured that the battery 3 to be inserted on the narrow side thereof in the embodiment shown can only be inserted in one position into the battery compartment 2, whereby an inadvertent mix-up of the positions of the first and second battery poles 6, 7 is prevented in a simple manner.

Figure 6:
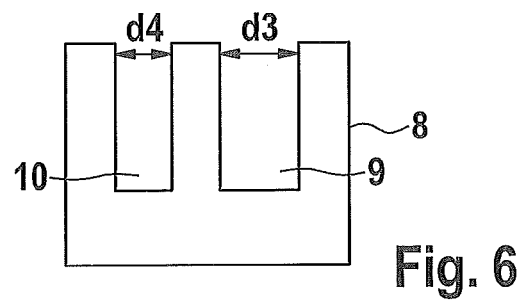
FIG. 6 is an alternative embodiment of a first side of the battery compartment in an embodiment having two slots.

FIG. 6 is an alternative embodiment of a first side 8 of the battery compartment 2 in an embodiment having two slots. The shown first side 8 of the battery compartment 2 has a first slot 9 and a second slot 10. In this embodiment, the battery 3 rests in the battery compartment 2 on the wide side of the battery, which is also illustrated in FIG. 2, such that one of the first and second battery poles 6, 7 can be contacted through a respective slot 9, 10. The first slot 9 has a diameter d3, and the second slot 10 has a diameter d4, which is smaller than diameter d3. As in the embodiment illustrated in FIG. 5, the diameters are dimensioned such that diameter d4 is larger than the diameter of the first battery pole 6, but smaller than the diameter of the second battery pole 7, while diameter d3 is larger than the diameter of the second battery pole 7. The second slot 10 having the smaller diameter d4 therefore allows only the first battery pole 6 to be received, but not the second battery pole 7, thereby effectively preventing incorrect insertion of the battery 3 in the battery compartment 2 of the pacemaker 1.

It will be apparent to those skilled in the art that numerous modifications and variations of the described examples and embodiments are possible in light of the above teachings. The disclosed examples and embodiments are presented for purposes of illustration only. Therefore, it is the intent to cover all such modifications and alternate embodiments as may come within the true scope of this invention.

We claim:

1. A pacemaker having a pacemaker housing, which comprises a recess in which a battery compartment displaceable between a removal position and an operating position along a first direction of displacement is disposed for receiving a replaceable battery having a first and a second battery pole disposed on a battery face through a removal side of the battery compartment, wherein the pacemaker comprises means for locking the battery compartment in the operating position, wherein on a first side oriented in the first direction of displacement, the battery compartment has at least one first slot, which is open toward the removal side of the battery compartment and positioned on the first side such that it allows contacting of the battery from outside of the battery compartment, wherein the battery compartment includes an electrically isolating partial cover, which is disposed on a second side opposite the first side and designed to cover a base of the battery directed toward the second side in the direction of the removal side of the battery compartment, and wherein the battery compartment has a first tension spring disposed on the second side, the first tension spring being designed to exercise a first spring force on the battery along the first direction of displacement.

2. The pacemaker according to claim 1, comprising a contact carrier, which is fastened in the pacemaker housing and mounted pivotally about a pivot axis and, which on a surface opposite of the first side of the battery compartment, has a first contact and a second contact on opposing sides of the pivot axis and is disposed such that the first batter pole and the second battery pole contacts one of the first contact and the second contact in the operating position of the battery compartment.

3. The pacemaker according to claim 1, wherein the first slot has a first diameter (d1) and a second diameter (d2), wherein the second diameter (d2) is smaller than the first diameter (d1), wherein the first slot has the first diameter (d1) at a first point and the second diameter (d2) at a second point, and wherein the first point is disposed at a lesser distance from the removal side than the second point.

4. The pacemaker according to claim 3, wherein the second diameter (d2) is larger than a diameter of the first battery pole and smaller than a diameter of the second battery pole and wherein the first diameter (d1) is larger than the diameter of the second battery pole.

5. The pacemaker according to claim 1, further comprising a second slot open toward the removal side of the battery compartment on the first side of the battery compartment, wherein the first slot is positioned on the first side such that it enables contacting of the first battery pole from outside of the battery compartment, and wherein the second slot is positioned on the first side such that it enables contacting of the second battery pole from outside of the battery compartment.

6. The pacemaker according to claim 5, wherein the first slot has a third diameter (d3) and the second slot has a fourth diameter (d4), wherein the fourth diameter (d4) is smaller than the third diameter (d3).

7. The pacemaker according to claim 6, wherein the fourth diameter (d4) is larger than a diameter of the first battery pole and smaller than a diameter of the second battery pole and wherein the third diameter (d3) is larger than the diameter of the second battery pole.

8. The pacemaker according to claim 1, wherein the battery compartment on the second side has a second tension spring and a handle which can be displaced along a second direction of displacement intersecting the first direction of displacement, wherein the second tension spring is designed to exercise a spring force on the handle along the second direction of displacement, wherein the recess of the pacemaker housing and the handle comprise at least one groove and a spring, wherein the groove has a closed part and a part which is open in the first direction of displacement, wherein the spring can be guided in the groove and is disposed such that the second tension spring exercises a second spring force on the handle when the spring is located in the open part of the groove, and exercises a third spring force on the handle when the spring is located in the closed part of the groove, wherein the second spring force is greater than the third spring force.

9. The pacemaker according to claim 8, wherein a connecting line from the open part of the groove to the closed part of the groove has a direction component in the first direction of displacement such that the second tension spring through the action of force thereof is designed to move the battery compartment into the operating position.

10. A pacemaker according to claim 1, wherein the second side of the battery compartment has a sealing ring surrounding the second side, the ring being designed to seal the recess of the pacemaker housing when the battery compartment is in the operating position.

11. The pacemaker according to claim 1, wherein the replacement battery includes a 9V battery.

\* \* \* \* \*